United States Patent
Ricci et al.

(10) Patent No.: US 10,835,652 B2
(45) Date of Patent: Nov. 17, 2020

(54) MAGNETICALLY-LEVITATED BLOOD PUMP WITH OPTIMIZATION METHOD ENABLING MINIATURIZATION

(71) Applicants: Worldheart Corporation, Miami Lakes, FL (US); Carnegie Mellon University, Pittsburgh, PA (US)

(72) Inventors: Michael R. Ricci, Camarillo, CA (US); James F. Antaki, Pittsburgh, PA (US); Josiah E. Verkaik, Lompoc, CA (US); David B. Paden, Goleta, CA (US); Shaun T. Snyder, Santa Barbara, CA (US); Bradley E. Paden, Goleta, CA (US); Jingchun Wu, Irvine, CA (US)

(73) Assignee: Worldheart Corporation, Miami Lakes, FL (US)

( * ) Notice: Subject to any disclaimer, the term of this patent is extended or adjusted under 35 U.S.C. 154(b) by 497 days.

(21) Appl. No.: 15/064,960

(22) Filed: Mar. 9, 2016

(65) Prior Publication Data
US 2016/0184499 A1    Jun. 30, 2016

Related U.S. Application Data

(63) Continuation of application No. 13/054,903, filed as application No. PCT/US2009/058251 on Sep. 24, 2009, now Pat. No. 9,314,557.
(Continued)

(51) Int. Cl.
*A61M 1/10* (2006.01)
*A61M 1/12* (2006.01)
*F16C 32/04* (2006.01)

(52) U.S. Cl.
CPC ............ *A61M 1/1015* (2014.02); *A61M 1/10* (2013.01); *A61M 1/101* (2013.01);
(Continued)

(58) Field of Classification Search
CPC .............. A61M 1/1015; A61M 1/1031; A61M 1/1034; A61M 1/122; A61M 1/0102;
(Continued)

(56) References Cited

U.S. PATENT DOCUMENTS

| 4,688,998 A | 8/1987 | Olsen et al. |
| 4,763,032 A | 8/1988 | Bramm et al. |

(Continued)

FOREIGN PATENT DOCUMENTS

| JP | H11303788 | 11/1999 |
| JP | 2003503639 A | 1/2003 |

(Continued)

OTHER PUBLICATIONS

International Search Report and Written Opinion dated Apr. 26, 2010 for PCT/US2009/058251, 12 pages.
(Continued)

*Primary Examiner* — Christopher Koharski
*Assistant Examiner* — Pamela M. Bays
(74) *Attorney, Agent, or Firm* — Christopher & Weisberg, P.A.

(57) ABSTRACT

A magnetically-levitated blood pump with an optimization method that enables miniaturization and supercritical operation. The blood pump includes an optimized annular blood gap that increases blood flow and also provides a reduction in bearing stiffness among the permanent magnet bearings. Sensors are configured and placed optimally to provide space savings for the motor and magnet sections of the blood pump. Rotor mass is increased by providing permanent magnet placement deep within the rotor enabled by a draw rod configuration.

9 Claims, 5 Drawing Sheets

Related U.S. Application Data

(60) Provisional application No. 61/100,655, filed on Sep. 26, 2008.

(52) U.S. Cl.
CPC ......... *A61M 1/1031* (2014.02); *A61M 1/1034* (2014.02); *A61M 1/1086* (2013.01); *A61M 1/122* (2014.02); *A61M 1/127* (2013.01); *F16C 32/0448* (2013.01); *F16C 2316/18* (2013.01); *Y10T 29/49012* (2015.01)

(58) Field of Classification Search
CPC .............. A61M 1/1086; A61M 1/1087; A61M 1/1008; A61M 1/1029; A61M 1/10; A61M 1/101
USPC .......................................................... 600/16
See application file for complete search history.

(56) References Cited

U.S. PATENT DOCUMENTS

| | | | |
|---|---|---|---|
| 4,846,152 A | 7/1989 | Wampler et al. | |
| 4,944,748 A | 7/1990 | Bramm et al. | |
| 5,078,741 A | 1/1992 | Bramm et al. | |
| 5,112,202 A | 5/1992 | Oshima et al. | |
| 5,195,877 A | 3/1993 | Kletschka | |
| 5,326,344 A | 7/1994 | Bramm et al. | |
| 5,329,603 A * | 7/1994 | Watanabe | G02B 6/3869 385/86 |
| 5,385,581 A | 1/1995 | Bramm et al. | |
| 5,443,503 A | 8/1995 | Yamane | |
| 5,470,208 A | 11/1995 | Kletschka | |
| 5,507,629 A | 4/1996 | Jarvik | |
| 5,695,471 A | 12/1997 | Wampler | |
| 5,725,357 A | 3/1998 | Nakazeki et al. | |
| 5,840,070 A | 11/1998 | Wampler | |
| 5,924,975 A | 7/1999 | Goldowsky | |
| 5,928,131 A | 7/1999 | Prem | |
| 6,183,412 B1 | 2/2001 | Benkowski et al. | |
| 6,201,329 B1 | 3/2001 | Chen | |
| 6,293,901 B1 | 9/2001 | Prem | |
| 6,368,083 B1 | 4/2002 | Wampler | |
| 6,447,266 B2 | 9/2002 | Antaki et al. | |
| 6,761,532 B2 | 7/2004 | Capone et al. | |
| 7,070,398 B2 | 7/2006 | Olsen et al. | |
| 8,376,926 B2 | 2/2013 | Benkowsi et al. | |
| 8,403,824 B2 | 3/2013 | Foster | |
| 8,550,975 B2 | 10/2013 | Foster | |
| 8,731,664 B2 | 5/2014 | Foster et al. | |
| 9,162,018 B2 | 10/2015 | Foster | |
| 2001/0031210 A1* | 10/2001 | Antaki | F04D 3/005 417/356 |
| 2003/0100816 A1* | 5/2003 | Siess | A61M 1/101 600/16 |
| 2003/0503639 | 7/2003 | Heilman et al. | |
| 2005/0107657 A1* | 5/2005 | Carrier | F04D 1/04 600/16 |
| 2005/0135948 A1 | 6/2005 | Olsen et al. | |
| 2005/0287022 A1* | 12/2005 | Yaegashi | A61M 1/101 417/420 |
| 2006/0024182 A1* | 2/2006 | Akdis | F04D 29/047 417/423.12 |
| 2006/0183962 A1 | 8/2006 | Okubo et al. | |
| 2006/0247486 A1 | 11/2006 | Mendler | |

FOREIGN PATENT DOCUMENTS

| | | |
|---|---|---|
| JP | 2004000484 A | 1/2004 |
| WO | 200102724 A1 | 1/2001 |

OTHER PUBLICATIONS

Supplementary European Search Report, corresponding European Application No. EP 09 81 6862, dated Jun. 13, 2017, 8 pages.

* cited by examiner

MAGNETICALLY-LEVITATED BLOOD PUMP WITH OPTIMIZATION METHOD ENABLING MINIATURIZATION

CROSS REFERENCE TO RELATED APPLICATIONS

This application is a continuation of U.S. application Ser. No. 13/054,903, filed on May 27, 2011 which claims the benefit of priority of U.S. Provisional Patent Application No. 61/100,655, filed Sep. 26, 2008, the disclosures of which are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract number HHSN262800448192C awarded by the National Institutes of Health.

FIELD OF THE INVENTION

The subject matter of the present disclosure generally relates to a pump having a magnetically-levitated rotor. More particularly, it relates to a blood pump used as a ventricular assist device (VAD) for providing cardiac assist. The invention enables miniaturization via supercritical operation of the spinning pump rotor. With this enhanced miniaturization, the VAD can be implanted in a less invasive surgical procedure or can be used with infants.

BACKGROUND OF THE INVENTION

Roughly 700,000 patients die from heart disease in the U.S. each year and 35,000 to 70,000 of these could benefit from mechanical circulatory support or a heart transplant. However, only about 2,500 transplant hearts become available each year. This translates to a profound need for a reliable mechanical blood pump to serve as a cardiac assist device or artificial heart.

Several prior-art devices attempt to solve this problem. Indeed, numerous embodiments of blood pumps exist, but are subject to significant operational problems. Several such prior-art pumps are discussed herein below.

In U.S. Pat. No. 4,688,998 issued to Olsen et al., a motor stator is disclosed that consists of C-shaped rings. The rings substantially increase the diameter of the pump contrary to the anatomical requirement of small size and weight.

In U.S. Pat. Nos. 4,763,032, 4,944,748, 5,078,741, 5,326,344, and 5,385,581, all issued to Bramm et al., a device is disclosed that requires two inflow channels, which increase the total blood-wetted surface. Among other things, this large contact area between artificial materials and the blood increases immune system response to the pump as well as the probability of thromboembolism. Further, connecting the two inlets of this particular pump to the heart is complex and requires additional tubing. Thus, anatomical interference of such pumps with natural organs and structures is increased.

In FIG. 31 of U.S. Pat. No. 4,944,748, there is also disclosed an axial-flow magnetically-levitated blood pump. However, a pump that offers minimal pump volume for a given flow is not disclosed. In particular, the embodiment of FIG. 31 depicts a narrow gap for blood flow between the rotor and the housing. While this is advantageous for magnetic bearing stiffness, it does not lead to a miniaturized pump. FIG. 31 of the '748 patent suggests a ratio of gap to rotor diameter of roughly 1/30 and there is no disclosure of a process for optimally choosing this gap. Nor is there a disclosure of a method of choosing the rotor speed, rotor inertias, and magnetic bearing stiffness in combination to achieve a miniaturized pump.

In U.S. Pat. No. 5,112,202 issued to Oshima et al., a device is disclosed in the form of a centrifugal pump that utilizes a magnetic coupling with mechanical bearings subject to wear. This pump is not suitable for long-term implantation as the bearings will eventually fail due to wear.

In U.S. Pat. Nos. 5,195,877 and 5,470,208 issued to Kletschka, a device is disclosed that requires two inflow channels, which increases the total blood-wetted surface. This large contact area between artificial materials and the blood increases immune system response to the pump. The large surface area also increases the probability of thromboembolism. Further, connecting the two inlets of the pump to the heart is complex and requires additional tubing. Thus, anatomical interference of the pump with natural organs and structures is increased.

In U.S. Pat. No. 5,443,503 issued to Yamane, a pump device is disclosed that has a jewel bearing. Such bearings are subject to wear in a long-term implant. Further, the jewel bearing is a point of blood stasis and is subject to clotting and may lead to thromboembolism. Washout holes are provided to counter such blood stasis, but such washout holes themselves increase the total blood-wetted surface and thus likely negating any benefit.

In U.S. Pat. No. 5,507,629 issued to Jarvik, a device is disclosed that includes a mechanical bearing in the form of a jewel bearing which is a point of blood flow stasis. The blood stasis point is a location of thrombus formation and a source of thromboembolism. Other embodiments of this invention levitate the rotor using only passive magnetic bearings that are inherently unstable, especially during the requisite high-speed rotor rotation. Unstable rotors can contact the pump housing and potentially stop the blood flow.

In U.S. Pat. Nos. 5,695,471 and 5,840,070, both issued to Wampler, a blood pump is disclosed. Wampler '471 is similar to the device of Jarvik '629 in that there is a stasis point at the jewel bearing. The stasis point is a site of thrombus formation and a source of thromboembolism. Further, the jewel bearing will eventually wear out and the impeller will cease to rotate. Wampler '070 uses a hydrodynamic thrust bearing. Such a bearing is highly inappropriate for use within blood processing because such bearings can damage the blood via the high mechanical shear that is inherent to such bearings.

In U.S. Pat. No. 5,725,357 issued to Nakazeki, a device is disclosed in the form of a pump that contains a motor with mechanical bearings subject to wear. Such a device is not suitable for a long-term implant as the mechanical bearings will eventually fail and cause the pump to stop working.

In U.S. Pat. No. 5,928,131 issued to Prem, an elongated pump is disclosed that exposes blood to large regions of foreign material and increases the likelihood of blood damage and thrombus formation. There is also a large region of high blood shear. Blood shear causes blood damage and can trigger undesirable clotting mechanisms in the body. Further, no manner is disclosed for choosing the blood gap, rotor inertias, rotor speed range, and magnetic bearing stiffness to achieve a miniaturized pump.

In U.S. Pat. No. 6,761,532 issued to Capone et al., an axial-flow magnetically-levitated blood pump is disclosed. However, no means for miniaturizing the pump is disclosed.

In particular, the embodiment of FIG. 2 of this patent depicts a narrow gap for blood flow between the rotor and the housing. While this is advantageous for magnetic bearing stiffness, it does not lead to a miniaturized pump. FIG. 2 of the '532 patent suggests a ratio of gap to rotor diameter of roughly 1/30 and there is no disclosure of a means for optimally choosing this gap nor is there a disclosure of choosing the rotor speed, rotor inertias, and magnetic bearing stiffness in combination to achieve a miniaturized pump. Moreover, the '532 patent places axial position sensor in such a way as to significantly elongate the pump.

Still further, several Ventricular Assist Device (VAD) systems have been developed over the years for bridge to implant, destination therapy, and as a bridge to recovery. A general understanding of such devices can be gained by reviewing the cardiac assist products of World Heart Inc. of Salt Lake City, Utah or Thoratec Corporation of Pleasanton, Calif.

From the discussion above, it becomes readily apparent that existing devices on the market are overly complex, prone to mechanical failure, promote thromboembolism and strokes, and otherwise suffer from shortcomings related to their ineffective designs. Moreover, none of these designs offer a combination of magnetic levitation and small size. None disclose the use of supercritical operation for miniaturization, nor do they disclose the design of rotor-to-housing gaps in combination with rotor mass, speed ranges, and bearing stiffnesses to achieve supercritical operation and small size. Further, none disclose a cable attachment and internal interconnection space supporting miniaturization.

Accordingly, it is desirable to provide for a new and improved, effective rotary blood pump suitable for long-term implantation into humans for artificial circulatory support. What is needed is such a blood pump that is highly reliable. What is also needed is such a blood pump that meets anatomical requirements with a very compact physical design. What is further needed is such a blood pump that minimizes blood-wetted surface area. Still, what is needed is such a blood pump that minimizes deleterious effects on blood and its circulatory system, the immune system, and other related biological functions. What is also needed is such a blood pump that is not only resilient to everyday accelerations and bodily movements, but also includes stable rotor dynamics, a high motor efficiency, high fluid efficiency, low power consumption for levitation, low vibration, low manufacturing costs, and increased convenience to the patient. Still further, what is needed is a blood pump that overcomes at least some of the disadvantages of the prior art while providing new and useful features.

SUMMARY OF THE INVENTION

The present invention provides a magnetically-levitated (maglev) blood pump suitable for use as a Ventricular Assist Device (VAD) that overcomes the deficiencies of the prior art.

In general, maglev blood pumps have a combination of feedback-controlled (or "active") magnetic bearings and permanent magnet (PM) magnetic bearings. PM magnetic bearings are inexpensive, energy-efficient, and low-cost but have relatively low stiffness compared to hydrodynamic bearings or active magnetic bearings. A challenge with the design of maglev blood pumps employing PM magnetic bearings for radial bearings is that resonances can occur in the range of operating speeds of the rotor used for pumping. The essentially rigid rotor mass, gyroscopic forces, and spring properties of the magnetic bearings work together to create these mechanical resonances of the rotor that, in general, depend on the rotor speed. A rotor speed at which a resonance is excited by imbalances in the rotor is called a "critical speed." When the rotor speed is above at least one critical speed, the operation is referred to as "supercritical operation." When the rotor speed is below all the critical speeds, the operation is referred to "subcritical operation."

It is desirable to avoid critical speeds in the normal operating speed ranges to avoid vibration and possible touchdown of the rotor to the housing. The present invention pertains to component sizing such that supercritical operation is consistent with effective pumping and miniaturization of the pump. In particular, the present invention uses a large gap between the housing and rotor. The large gap in itself increases the flow. Moreover, the present invention uses the larger gap to lower the stiffness of the PM magnetic bearings and hence lower the critical speeds. As a consequence, the entire range of desired pump speeds lies above the rotor critical speeds. Advantageously, high rotor speeds in combination with the large gap allow for high flows in a small pump according to the present invention. Because the present invention is designed for supercritical operation, increasing the rotor mass is possible while simultaneously increasing the speed range of operation at the low end. Thus, the proportion of motor mass and PM magnet mass in the rotor can be made larger (e.g., by using the space in the commonly hollow rotor designs) and the mass in the housing can be smaller. Accordingly, the housing size is reduced and the overall pump size is reduced.

In one implementation, the invention is directed at supporting the smallest of human patients as a bridge to transplant. In yet another implementation, the invention can be adapted as a minimally invasive system for providing cardiopulmonary support for adults.

The present invention has multiple implementations and applications. The maglev axial mixed-flow ventricular assist device according to the present invention is directed towards having the following benefits: fully maglev system without any contacting parts during normal operation; miniaturization though large rotor-to-housing gap and supercritical operation; streamlined blood flow with minimal blood damage and thrombus formation; miniaturization for use in adults, children, and infants; miniaturization to enable minimally-invasive implantation; high reliability due to negligible wear; and minimized power requirement due to large flow gaps.

In a first aspect of the invention, there is provided a magnetically-levitated blood pump, the blood pump including: an inflow end providing for entry of blood; an outflow end providing for exit of the blood; a stator oriented in axial alignment with, and located between, the inflow end and the outflow end, and including at least one stator permanent magnet and a motor coil; a rotor centered within the stator, and including a plurality of rotor permanent magnets; at least one permanent magnet bearing formed from a first portion of the at least one stator permanent magnet and a first corresponding portion of the rotor permanent magnets; a motor magnet for interaction with the motor coil, and formed from a second corresponding portion of the rotor permanent magnets; and an annular blood gap formed between an outermost surface of the rotor and an innermost surface of the stator, where a ratio of the annular blood gap to rotor diameter is greater than 1/10.

In a second aspect of the invention, there is provided a magnetically-levitated blood pump, the blood pump including: an inflow end providing for entry of blood; an outflow end providing for exit of the blood; a stator oriented in axial alignment with, and located between, the inflow end and the outflow end, and including a plurality of stator permanent magnets, at least one voice coil, and a motor coil; a rotor centered within the stator, and including a plurality of rotor permanent magnets; a first permanent magnet bearing arranged near the inflow end, and formed from a first portion of the stator permanent magnets and a first corresponding portion of the rotor permanent magnets; a second permanent magnet bearing arranged near the outflow end, and formed from a second portion of the stator permanent magnets and a second corresponding portion of the rotor permanent magnets; a motor magnet for interaction with the motor coil, and formed from a third corresponding portion of the rotor permanent magnets; and a fourth corresponding portion of the rotor permanent magnets for interaction with the at least one coil, the at least one voice coil configured to additionally interact with the first corresponding portion of the rotor permanent magnets.

In a third aspect of the invention, there is provided a method of optimizing a magnetically-levitated blood pump, the method including: providing a rotor for the blood pump with a plurality of permanent magnet rings configured to increase rotor mass; providing stator permanent magnets located on a stator, the stator permanent magnets corresponding to a portion of the plurality of permanent magnet rings, the stator permanent magnets and the plurality of permanent magnet rings forming magnetic bearings having a reduced stiffness; and configuring the rotor and the stator to enable the reduced stiffness.

In a fourth aspect of the invention, there is provided a method of optimizing a magnetically-levitated blood pump for supercritical operation, the method including: providing a stator oriented in axial alignment with, and located between, an inflow end providing for entry of blood and an outflow end providing for exit of the blood, and including a plurality of stator permanent magnets, at least one voice coil, and a motor coil; providing a rotor centered within the stator, including a plurality of rotor permanent magnets, and configured to provide a ratio of rotor diameter to an outflow end diameter of less than 2; and providing a first permanent magnet bearing and a second permanent magnet bearing, the first permanent magnet bearing arranged near the inflow end and formed from a first portion of the stator permanent magnets and a first corresponding portion of the rotor permanent magnets, the second permanent magnet bearing arranged near the outflow end and formed from a second portion of the stator permanent magnets and a second corresponding portion of the rotor permanent magnets, and the first and second permanent magnet bearing having a reduced stiffness enabled by a gap configuration formed between the rotor and the stator.

Other advantages and benefits may be possible, and it is not necessary to achieve all or any of these benefits or advantages in order to practice the invention as claimed. Therefore, nothing in the forgoing description of the possible or exemplary advantages and benefits can or should be taken as limiting.

BRIEF DESCRIPTION OF THE DRAWINGS

The invention, both as to organization and methods of operation, together with further objects and advantages thereof, may best be understood by reference to the following description, taken in conjunction with the accompanying drawings in which.

DETAILED DESCRIPTION

As utilized herein, terms such as "about", "approximately", "substantially" and "near" are intended to allow some leeway in mathematical exactness to account for tolerances that are acceptable in the trade.

Before explaining the present invention in detail, it should be noted that the invention is not limited in its application or use to the details of construction and arrangement of parts illustrated in the accompanying drawings and description. The illustrative embodiment of the invention may be implemented or incorporated in other embodiments, with or without variations and modifications, and may be practiced or carried out in various ways without straying from the intended scope of the present invention. Furthermore, unless otherwise indicated, the terms and expressions employed herein have been chosen for the purpose of describing the illustrative embodiment of the present invention and should not be construed as limiting the intended scope of the present invention. Further, it is understood that any one or more of the following-described embodiments, expressions of embodiments, examples, methods, . . . etc. can be combined with any one or more of the other following—described embodiments, expressions or embodiments, examples, methods, . . . etc.

Figure 1:
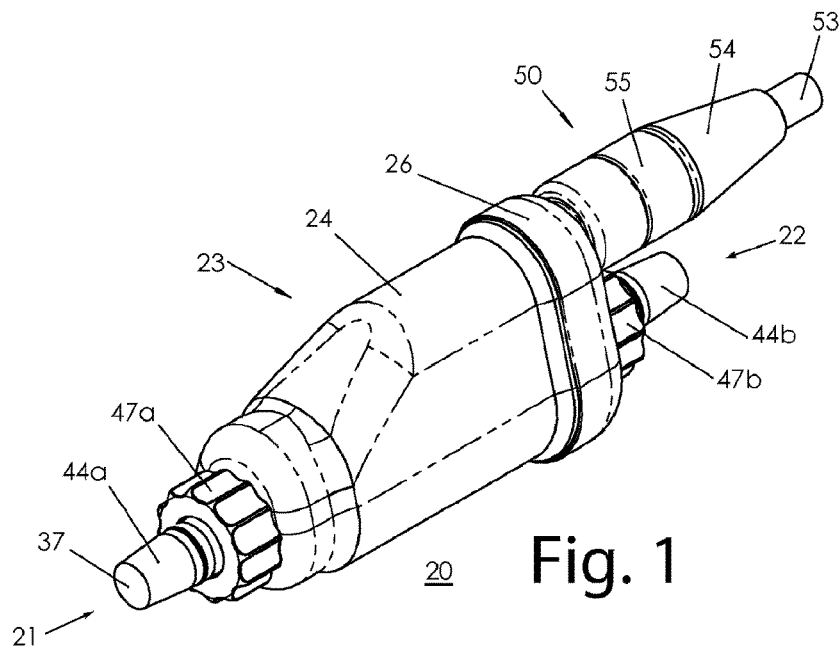
FIGS. 1 through 4 show, respectively, a perspective view, top view, front-end view, side view, and back view of the preferred embodiment of the present invention in a fully assembled configuration.

FIG. 1 shows a perspective view of the blood pump 20 in accordance with the preferred embodiment of the present invention. As seen from the outside, the blood pump is an axial system with an inflow end 21 and outflow end 22. Conduit adaptors 44a and 44b, fastened respectively by adaptor nuts 47a and 47b, are provided at both ends for attachment of the blood pump 20 to an inflow cannula at the inflow end 21 and an outflow cannula at the outflow end 22 (cannulas not shown). The blood pump 20 is encased by an exterior housing comprising an exterior housing cover 23 and a housing end cap 26. The exterior housing has a dome 24 to accommodate an axially-oriented cable feed through assembly 50. The dome structure 24 also accommodates the electrical interconnections to the blood pump 20, enables anatomic fit, simplified surgical procedures, and overall miniaturization. It should be readily understood within the context of the invention that the exterior housing cover 23 could optionally be reversed with the housing end cap 26 and cable feed through assembly 50 oriented in reverse on the inflow end 21.

Also shown in FIG. 1 is the inflow lumen 37 through which blood flows, the cable assembly 53 for the electrical interconnections to the internal workings of the blood pump 20. That is to say, such electrical interconnections carry sensor signals from the levitation system, and power to the motor and levitation system. The cable and its terminations which form the cable assembly 53 are protected by an elastic strain relief boot 54. A retention ring 55 clamps the strain relief boot 54 to an underlying connector structure.

Figure 2:
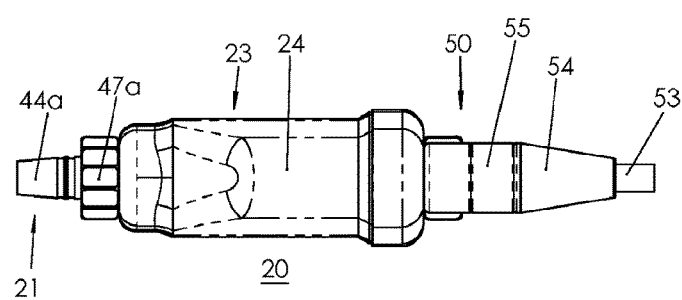
Figure 3:
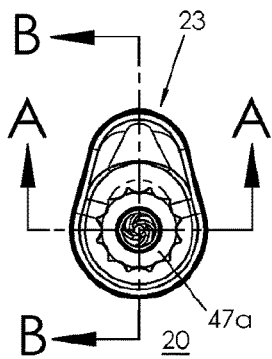
Figure 4:
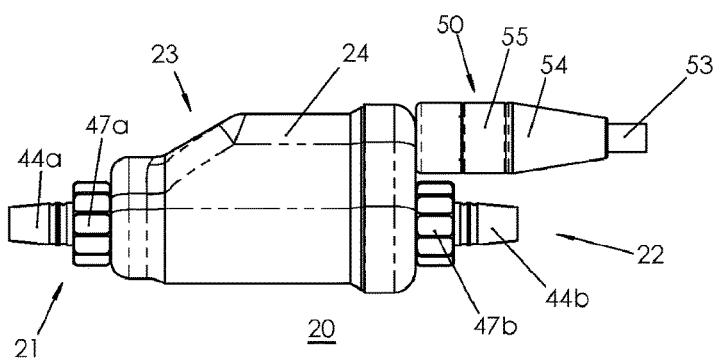

FIG. 2 is a top view of the blood pump 20 showing features as described above in the discussion of FIG. 1. Here, the inflow end 21 is evident while the outflow end is hidden from view beneath the cable feed through assembly 50. Likewise, FIG. 3 is a front-end view of the blood pump 20 and FIG. 4 is a side view of the blood pump 20 each showing features as described is the discussion of FIG. 1. It should be noted that the slim profile of the present inventive blood pump 20 as clearly seen by FIGS. 2 through 4 assures anatomic fit and simplified surgical procedures. The asymmetric shape of the pump housing cover 23 visible in FIGS. 1, 3, and 4 enables minimal use of space for accommodation of internal components thus minimizing the size of the system.

Figure 5:
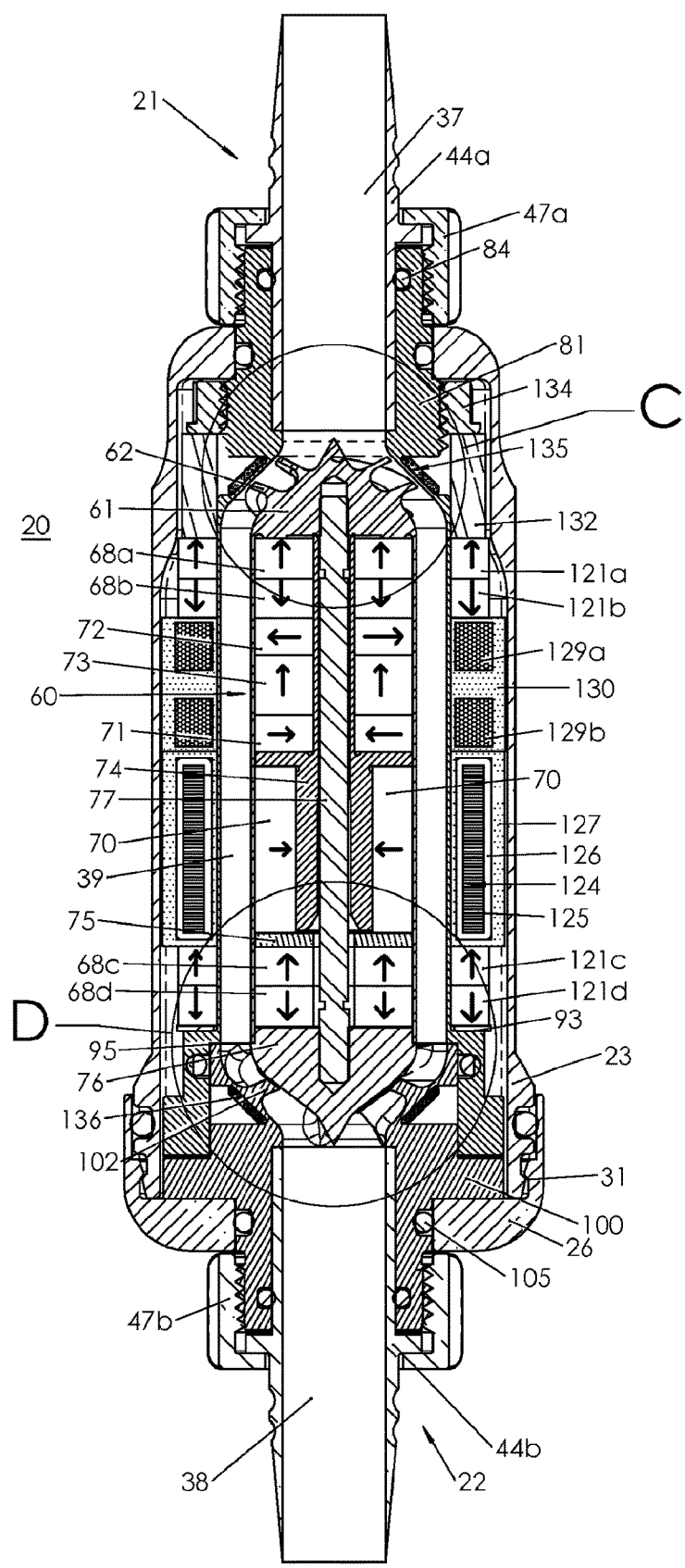
FIG. 5 is a lengthwise, cross-sectional top view taken along cross-section line A-A of FIG. 3.

FIG. 5 is a section view of the blood pump 20 corresponding to the cross-section taken across line A-A indicated in FIG. 3. In addition to the external features shown in FIG. 1, the internal features of the blood pump 20 are shown in FIG. 5 and described as follows. As shown, blood flow is designed to flow in the direction from inflow lumen 37 to outflow lumen 38 and thereby respectively guide the blood flow into and out of pump. The rotor assembly 60 spins and pumps blood via attached impeller blades 62. Stationary stator blades 102 direct the flow at the outlet end 22 of the blood pump 20. The rotor assembly 60 is rotated via a 4-pole motor assembly 124 forming stator components including motor iron 125, motor windings 126, and potting material 127 and rotor components including motor magnets 70. An advantage of a 4-pole motor design is that the rotor magnets collectively have no net dipole moment (up to manufacturing variations) so that there is minimal residual torques due to interactions with fields created by the PM stator magnets. 2-pole motors do not have this property, while 2N-pole motor do have this property when the integer N is greater than or equal to 2. Motor rotor magnets which collectively have nearly zero net dipole moment provide the benefit of reduced excitation of unwanted rotor motion at critical speeds.

FIG. 5 also shows radial support to the rotor assembly provided by fore and aft PM magnetic bearings. The fore PM magnetic bearing includes rotor PM rings 68a and 68b and corresponding stator PM rings 121a and 121b. Similarly, the aft PM magnetic bearing includes rotor PM rings 68c and 68d and corresponding stator PM rings 121c and 121d. The magnetization directions of the various permanent magnet components are indicated with arrows. Although two PM rings are shown in both the fore and the aft PM magnetic bearings, it should be readily apparent that the number of rings used in the PM magnetic bearings can vary without straying from the intended scope of the present invention. Likewise, various directions of magnetization can be used in the PM magnetic bearings as is known in the art such as, but not limited to, Halbach arrays. Still further, the magnetic intensity may vary from magnet type to magnet type and therefore the specific shape and size may vary from the specific embodiment shown without straying from the intended scope of the present invention.

While the fore and aft PM magnetic bearings provide a radial magnetic spring force that stabilizes and centers the rotor assembly 60 with a positive spring characteristic, the PM magnetic bearings also create a negative spring characteristic in the axial direction which makes the rotor axially unstable. To compensate for the axial negative spring characteristic, a feedback-controlled voice-coil actuator acts on the rotor assembly 60 in the axial direction. It should be understood that for applications of the present invention for short-term blood pump implants a passive mechanical structure can be used in lieu of a voice coil such as a jewel bearing or a ball and cap structure to counter axial forces. However, long term implants would preferably benefit from the non-mechanical voice coil arrangement of the preferred embodiment.

The voice-coil actuator is comprised of voice coils 129a and 129b wired such that current flows in opposite directions in the two coils 129a, 129b and thus interacts with magnets 71, 72, and 73 to produce an axial force in response to an electronically-controlled current in the coils 129a, 129b. Magnet 68b also contributes to the function of the voice-coil actuator as it is proximal to voice coil 129a and contributes to the radial magnetic field in voice coil 129a. The use of magnet 68b in both the fore PM magnetic bearing and the voice-coil actuator improves electrical power efficiency. The aspect of the present invention regarding this integration of the magnetic bearing function and the voice-coil actuator function is referenced as "incorporating an integrated PM bearing and voice-coil actuator."

Feed-back control of the voice-coil actuator in FIG. 5 is accomplished by using fore and aft position sensor coils 135 and 136. As the rotor assembly 60 moves fore and aft, the impedance of coils 135 and 136 change and the impedance change is interpreted as positional change by electronics external to the blood pump 20. A feedback control algorithm such as virtually zero power control (as described by J. Lyman, "Virtually zero powered magnetic suspension," U.S. Pat. No. 3,860,300, 1975 and incorporated herein by reference) is applied to the position signal to determine the voltage or current applied to the voice coils 129a and 129b. The motor windings 126 and motor iron 125 are encapsulated in potting material 127 for structural stability and improved heat transfer. Similarly, the voice coils 129a and 129b are encapsulated in a potting material 130 for the same reasons. The positioning the sensor coil 135 at the flow divergence adjacent to the impeller blades 62 makes use of this space that is not suitable for the motor, PM magnetic bearings, or voice coil actuator. Thus, this design enables a shorter and more compact pump design relative to one where the volume near the flow divergence is not used. Similarly, the positioning of the sensor coil 136 at the flow convergence adjacent to the stator blades 102 is advantageous for the same reason. This aspect of the present invention related to the placement of these sensor coils 135, 136 is referenced respectively as "located at a blood flow convergence/divergence."

Figure 10:
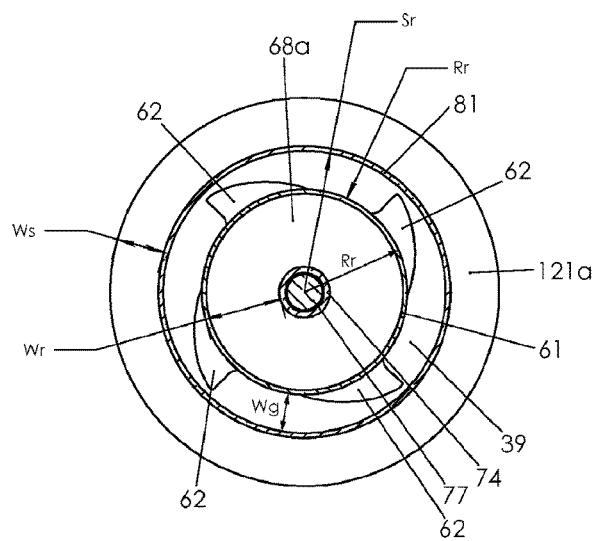
FIG. 10 is a cross-sectional view taken along cross-section line E-E in FIG. 9.

With further regard to FIG. 5, the stator housing 81 extends for a large fraction of the length of the blood pump 20. Stator housing 81 forms the outside wall of annular flow gap 39 which is a large part of the blood flow path through the pump. The radial dimension of the flow gap 39 is denoted Wg as depicted in FIG. 10. Additionally, the stator housing 81 supports the stator PM rings 121a, 121b, 121c, 121d, the potted voice coils 129a, 129b, the potted motors coils 126 and motor iron 125. These components are stacked and clamped in place using stator nut 134, collar 132, and end shoulder 93. Spacers may be placed throughout the stack to ensure accurate alignment with corresponding components in the rotor assembly. Collar 132 incorporates a slot (shown as element 133 in FIG. 6) enabling the connection of sensor coil 135.

Inflow conduit adaptor 44a is attached using nut 47a and a seal between the adaptor 44a and the stator housing 81 is formed with an O-ring 84. O-ring 105 is shown and additional O-ring seals are similarly indicated in cross-section but are not labeled for clarity of illustration. While the embodiment as shown uses O-ring seals, it should be readily apparent that welded elements may also be used for producing a compact and sealed housing. Exterior housing cover 23 and housing end 26 enclose the components mounted on the stator housing 81. The housing cover 23 and the housing end 26 snap together with snap fit lip 31. Outlet housing 100 incorporates the stationary stator blades 102. The outlet housing 100 also includes a stopping face 95 formed at the point of abutment between the stator housing 81 and the outlet housing 100. The stopping face 95 (seen more clearly in FIG. 8) is narrow relative to the total cross-section of the outlet housing 100. This relatively narrow, short dimension allows the stator blades 102 to more easily be machined from the end of the outlet housing 100. This enables the low-cost machining of the stator blades 102 and we describe this feature of the pump as having a "short housing end." The outlet housing 100 is clamped to the stator housing 81 in the axial direction with the tension in the snap fit lip 31. The outlet conduit adaptor 44b is clamped to the outlet housing 100 with nut 47b.

Also shown in FIG. 5 are the details of the rotor assembly 60. Here, the impeller housing 61 can be seen to include the impeller blades 62 and a deep cup structure than encloses the various permanent magnets (68a, 68b, 68c, 68d, 70, 71, and 72) used in the motor, voice-coil actuator and the PM magnetic bearings as well as spacer 75. The impeller housing is capped with a rotor tail 76 that fits on the interior of the cupped section of the impeller housing 61 and is held fast with a draw rod 77. Such assembly for enclosing magnets for the motor, magnetic bearings, and voice-coil actuator is referenced as a "draw-rod assembly". It is understood that the rotor tail 76 may additionally be laser-welded to the interior of the cupped section of the impeller housing 61. All of the rotor assembly magnets are mounted on the hub support 74. It should be understood that the fore-to-aft order of the motor and voice-coil actuator can be inverted on the rotor without straying from the intended scope of the present invention.

The conduit (or cannula) adapters 44a, 44b are attached to the inflow end 21 and outflow end 22 of the stator. Each cannula adaptor has a conical tapered end for securing a cannula or graft, a central flange and a cylindrical portion on the other side adapted for insertion from the inflow end and outflow end of the pump. The central flange of either adaptor includes a ferromagnetic ring affixed within and to affect a magnetic coupling to the housing when the flange is brought into co-axial proximity with the pump housing.

The numbered elements shown and described with regard to FIG. 5 are likewise shown throughout the remaining FIGS. 6 to 10.

Figure 6:
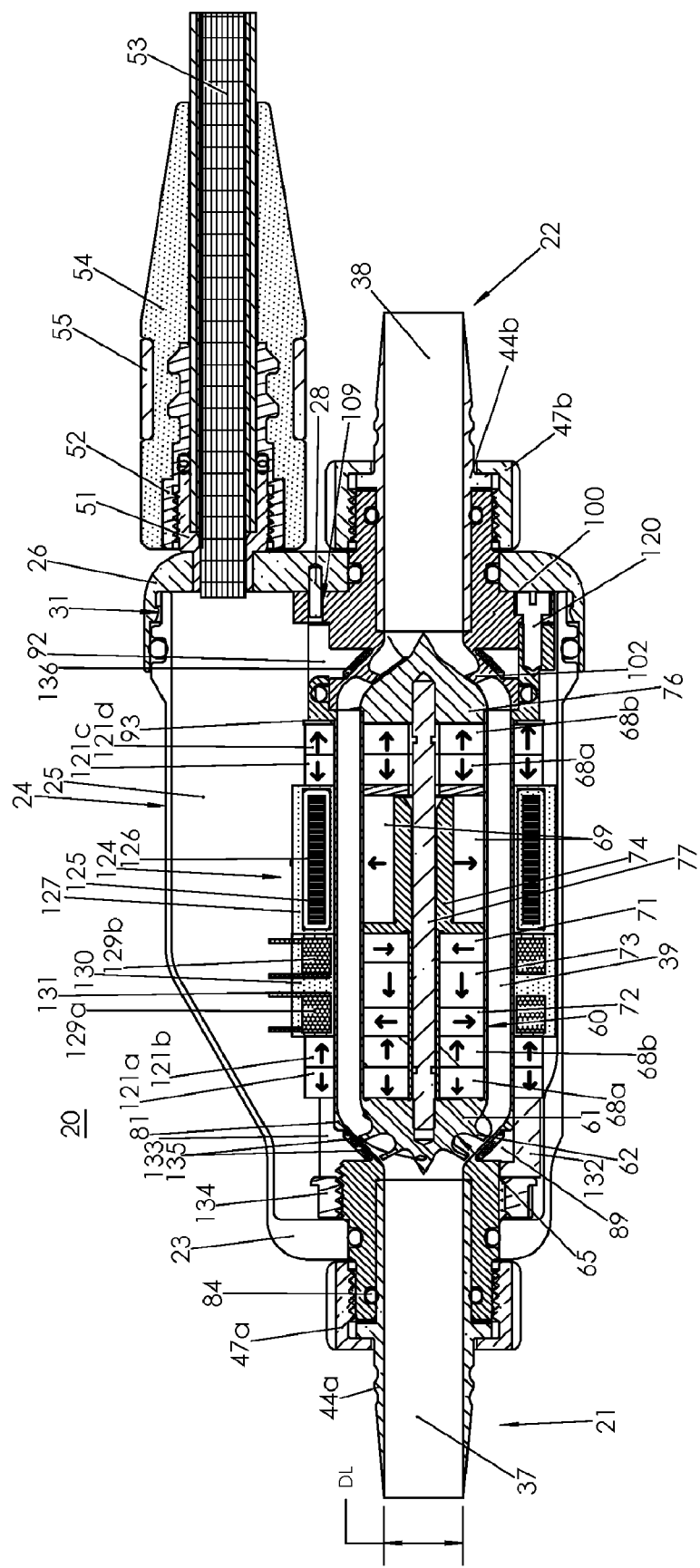
FIG. 6 is a lengthwise, cross-sectional side view taken along cross-section line B-B of FIG. 3.

FIG. 6 is a section view corresponding to cross-section taken across line B-B of FIG. 3 and shows the interface of the cable assembly 53 in relation to the blood pump 20 via a dome 24 in the exterior housing cover. The cable assembly 53 carries conductors for interconnection (not shown) through cavity 25 to the voice coils 129a, 129b, sensor coils 135, 136, and the motor windings 126. It should be understood that such manner of conductor interconnection is well known within the electrical art and not further described herein. The two voice coils 129a, 129b have four terminations shown—one of which is labeled 131. The motor and sensor coil terminations are not shown, but are similarly configured as is known in the electrical art. In addition, FIG. 6 shows the slot 133 in the standoff collar 132 through which the sensor coil interconnections are made. Similarly, slot 92 is shown in the housing end 100. Additional features of the cable assembly 53 are the feed-through body 51 which is press-fit into the housing end cap 26, and the feed-through nut 52. Pin 28 in pinhole 109 locks the relative orientation of the outlet housing 100 to the housing end cap 26. Screw 120 fastens the outlet housing 100 to the stator housing 81. Magnets 69 of the four-pole motor are oriented outward, and the diverging face of the impeller 65 is indicated.

Figure 7:
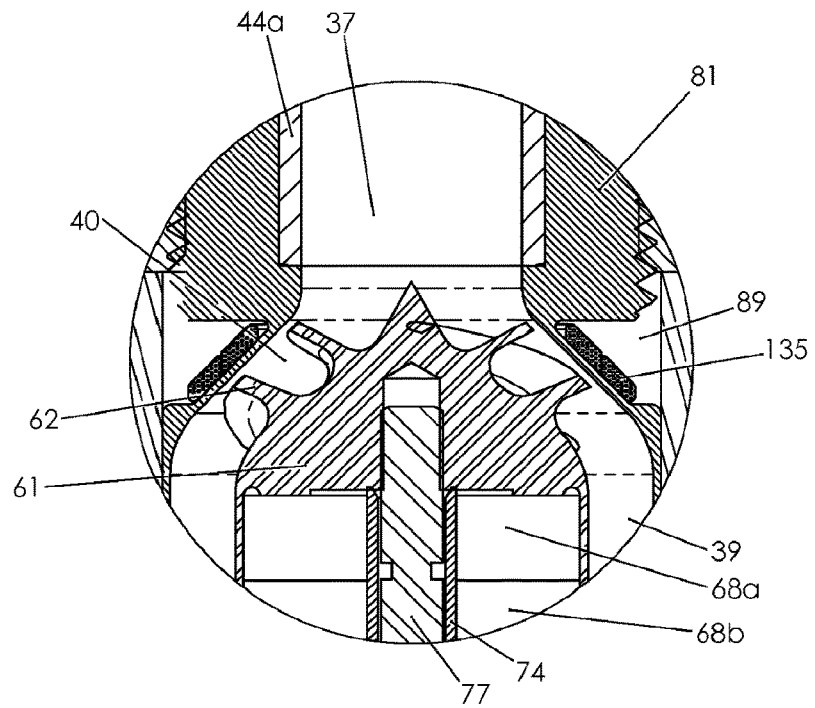
FIG. 7 is an enlarged detail view of the preferred embodiment corresponding to detail circle labeled C in FIG. 5.
Figure 8:
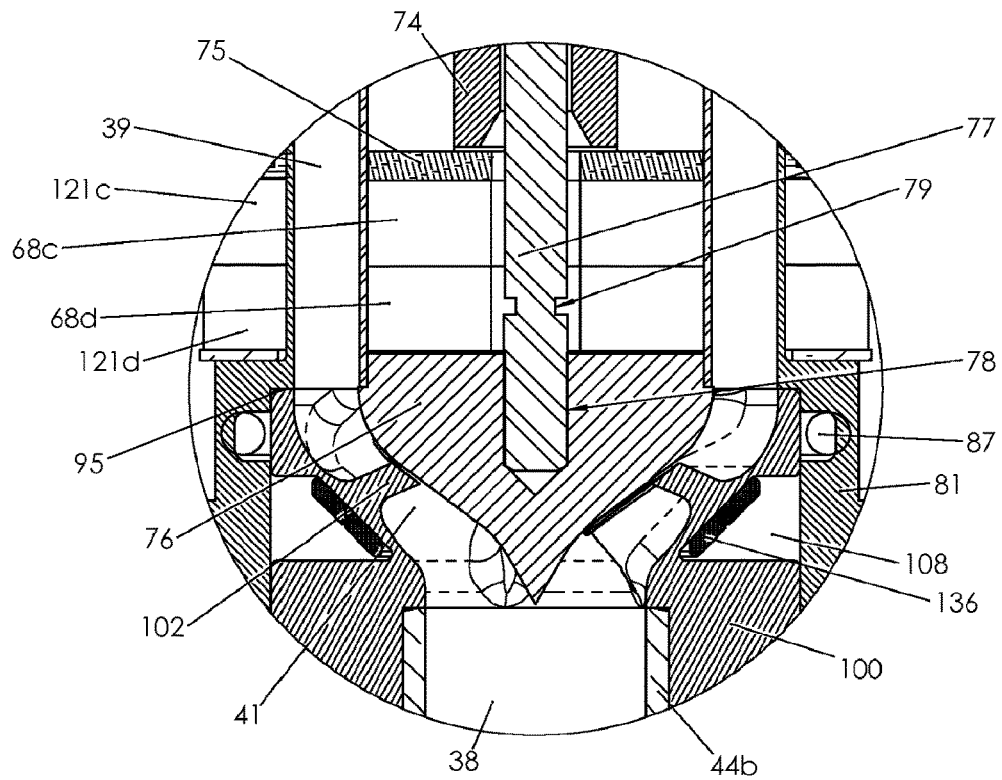
FIG. 8 is an enlarged detail view of the preferred embodiment corresponding to detail circle labeled D in FIG. 5.

FIGS. 7 and 8 are respective detail views C and D as indicated in FIG. 5 showing the inlet and outlet paths of blood flow. The inlet path of FIG. 7 shows the impeller blades 62 detailed relative to the sensor coils 135 which are wound in groove 89. Likewise, the outlet path of FIG. 8 shows the stator blades 102 detailed relative to the sensor coils 136 wound in groove 108. The sensor coils 135, 136 are of a truncated cone shape as shown in order to maximize their fractional change in impedance due to rotor motion. Alternatively, grooves 89 and 108 can be filled completely with wire with only that part of the coil closest to the rotor assembly 60 having a conical shape. In either case, the sensor coils 135, 136 are referenced as being "cone-shaped." FIG. 8 shows the draw rod 77, threads 78 (not detailed), and thread relief 79 used to assemble and fasten the rotor elements. In both FIGS. 7 and 8, the annular flow gap 39 is visible relative to the inflow lumen 37 and outflow lumen 38. From this detail, it should be readily apparent that the annular flow gap 39 is a relatively large gap approximately equivalent to the radius of lumens 37, 38.

Figure 9:
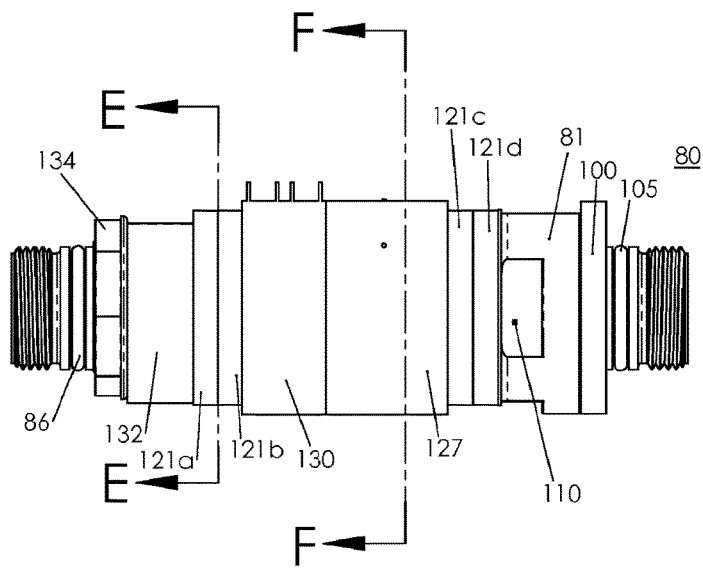
FIG. 9 is a side view of the stator according to the preferred embodiment with outer housings and cannula adaptors removed.

FIG. 9 is a side view of the stator assembly 80 according to the preferred embodiment with the exterior housing cover and cannula adaptors removed. In this view, O-rings 86 and 105 are visible. Additionally, stator nut 134 threaded onto stator housing 81 is shown at the left side of FIG. 9. The stator nut 134 clamps a stack of components between itself and the housing 81. The stack is comprised of (from left to right) collar 132, stator PM rings 121a and 121b, voice coil potting 130 (containing voice coils), motor potting 127 (containing motor iron and motor windings), and stator PM rings 121c and 121d. Outlet housing 100 is also shown. A standoff collar 110 is used to provide a window for routing conductors from the stator inlet sensor coils. A slot (not shown) is cut out of the housing 81 at the outflow end (at the right side of FIG. 9) to provide a window for routing the conductors from the stator outlet sensor coils.

FIG. 10 is a section view corresponding to the cross-section taken across line E-E of FIG. 9. A portion of the impeller blades 62 are visible in this cross-section within the annular flow gap 39. Also shown are the stator PM ring 121a, annular flow gap dimension Wg, stator PM ring radial width Ws, rotor PM ring 68a, rotor PM ring radial dimension Wr, rotor outside radius Rr, stator inside radius Sr, stator housing 81, the impeller housing 61, draw rod 77, and hub support 74.

Figure 11:
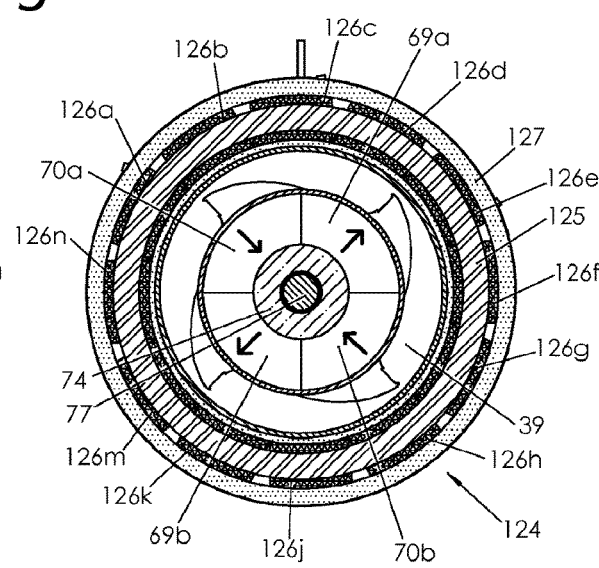
FIG. 11 is a cross-sectional view taken along cross-section line F-F in FIG. 9.

FIG. 11 is a cross-section view taken across line F-F in FIG. 9 showing the cross-sectional details of the motor assembly 124. The largest diameter component shown is the motor potting 127. Working inward, the next adjacent components are the twelve motor windings 126a to 126n for this 3-phase 4-pole motor configuration which are wound in a toroidal fashion around the motor iron 125. A layer of potting material appears on the inside of the coils and then interior to that is the stator housing and the annular flow gap 39. Interior to the rotor are shown the outwardly magnetized magnets 69a and 69b and the inwardly magnetized magnets 70a and 70b which are mounted on the hub support 74. Draw rod 77 is at the center of the FIG. 11.

Although the voice-coil magnets 71, 72, and 73 are shown throughout the figures in a particular magnetization, the reverse magnetizations to those shown may serve the purpose of creating a magnetic field at the coils 129a, 129b with a radial component that is inward for one of the coils and outward for the other. Other magnetic assemblies are also possible without straying from the intended scope of the present invention including, but not limited to, those with ferrous materials such as iron.

According to operation of the preferred embodiment, the maglev VAD includes an actively-controlled axial suspension and a passive radial suspension. PM bearing rings 68a, 68b, 68c, and 68d near each end of the rotor interact with PM bearing rings 121a, 121b, 121c, and 121d on each end of the stator housing 81 to maintain the rotor in a coaxial relationship with the stator inlet and outlet housing. In simple terms, the PM bearings serve as springs that support the rotor in the radial direction. This mass-spring system can oscillate in a number of modes and corresponding modal frequencies determined by the stiffnesses of the PM magnetic bearings, the mass and rotational inertias of the rotor, and the rotor speed (due largely to gyroscopic effects). As the rotor speed varies, inertial and magnetic imbalances, can cause vibrational motions of the rotor with the rotor speed is at or near a modal frequency called a critical speed. These large motions, in turn, can cause the impeller blades 62 or stator blades 102 to rub, respectively, against the stator housing 81 and/or rotor tail 76. Such rubbing or touchdown is undesirable so that operation near the critical speeds is to be avoided.

By choosing the mass of the rotor sufficiently large, choosing the stiffness of the PM magnetic bearings sufficiently small (largely by increasing the fluid gap Wg and hence the magnetic gap Sr minus the rotor radius Rr in FIG. 10), and choosing the speed range of the rotor to include speeds above at least one critical speed, the inventive blood pump can be designed of significantly reduced size relative to the prior art. Such a magnetically-levitated blood pump in accordance with the present invention whose pumping range includes speeds above at least one critical speed is called a supercritical maglev pump. The present invention is advantageous in that increasing the magnetic gap Sr minus Rr enables an increase in the fluid gap Wg and impeller blade height which, in turn, increases the pump flow at a given size. This synergy of combination elements of the present invention provides that all critical speeds for this rigid rotor configuration are below the operating range of the pump. Thus, the critical speeds do not limit the maximum speed of the pump and a very large range of operation is possible. Further, the large fluid gap and high rotor speeds work together to achieve very high flow rates in a small pump configuration. Ratios of fluid gap to rotor diameter Wg/(2Rr) greater than 1/10 (and as high as 1/5.4) combined with supercritical operation are achievable.

The miniaturization achieved with a large fluid gap combined with supercritical operations is revealed in other parameters in the pump configuration as well. The ratio of rotor diameter to cannula diameter (equal to inlet or outlet diameter) can be less than 2. As well, the rotor can have an relatively high average density. As part of the optimized configuration in accordance with the present invention, the magnetic bearing stiffness should be chosen sufficiently high so that under accelerations, due to motion of the patient for example, the rotor does not contact the housing.

One approach to optimizing the inventive configuration for supercritical operation is to provide for rotor inertias sufficiently large and/or the magnetic bearing stiffness sufficiently small (e.g., by choosing a large Wg) such that the critical speeds are below the speed range needed to accomplish the desired flow range. Further, as the pump passes through the critical speed, there is often vibration in the rotor so the blade tip clearance and the rotor damping are provided to be sufficiently large so as to avoid contact between the blade tips and the housing as the rotor speed passes through a critical speed. The formal process of analysis of rotor critical speeds is accomplished through a matrix vibration equation involving the mass matrix, stiffness matrix, damping matrix, and gyroscopic matrix for the system. This matrix vibration equation is uniquely combined with the motor and pump design in this system to achieve high overall pump efficiency. More specifically, the dynamics of the rotor are given by:

$$m\ddot{q}+(C+G(\Omega))\dot{q}+K_q=f(t)$$

Where q is a vector of which components are translations and rotations of the rotor excluding axial translation and rotation about the rotor axis. That is, q, captures the four expected vibrational motions of the rotor—two directions normal to the axis of rotation together with pitch and yaw motion of the rotor. M is corresponding mass matrix modeling the mass and rotational inertias, C is the damping matrix, $\Omega$ is the rotor angular velocity or speed, $G(\Omega)$ is the speed dependent gyroscopic matrix, K is the rotor stiffness matrix due to the PM magnetic bearings, and f(t) is the rotor forcing due to inertial and magnetic imbalances. During the design process, the damping C is assumed to be small or simply ignored when solving for the eigenvalues of the homogeneous equation (i.e., f(t) set equal to zero). These speed-dependent eigenvalues determine the critical speeds where large rotor motions can occur.

The pump magnetic and mechanical designs directly affect the matrix vibration equation. For example, adding rotor mass increases components of the mass matrix M, increasing the PM bearing gap generally decreases components of the stiffness matrix, K, and improving the rotor mechanical balance and magnetic balance reduces the rotor forcing f(t). If the magnetic materials do not have uniform magnetizations or if the magnetic fields are non-uniform due to mechanical imperfections, disturbance forces can be imposed on the rotor which we refer to as magnetic imbalance. Further, the gap 39 shared by the PM magnetic bearings, motor, voice-coil actuator, and pump is one source of design interaction. That is, the gap 39 affects the performance of all of these subsystems. The overall design of the pump is accomplished through the computer optimization of pump efficiency subject to constraints on size, flow rate, and speed relative to the critical speeds. A unique feature of the design optimization is that the motor speed is constrained to be greater than at least one of the critical speeds.

Control of the maglev VAD in accordance with the present invention is configured to facilitate continuous levitation of the rotor with minimal power dissipation. The active axial suspension is accomplished by the thrust coil assembly of the stator maintaining the rotor in a fixed axial position with respect to the stator inlet and outlet housing. This active suspension relies on a signal provided by the eddy current type sensor coils on the inlet end and outlet end to determine the shift in rotor position in an instant in time. The signal from the inlet sensor coils and the signal from the outlet signal coils are combined in a differential fashion to minimize noise and coupling to the thrust coils. The inlet and outlet sensor coils may be single coils or preferable comprised of two counter-wound coils to further reduce noise and coupling.

It should be understood that a control system (external to the blood pump) provides current to the thrust bearing coils and energizes them as appropriate for correcting the rotor position in an instant of time. Depending on the direction of current through the axial thrust coils, this will cause either a forward thrust or backward thrust as the magnetic field caused by the energized thrust coils will interact with the magnetic thrust bearing elements within the rotor. As already discussed, the axial thrust coil assembly may include two coils that are encased in a thermally conductive and electrically insulation potting. The motor components of the stator and rotor are also displaced between the radial suspension elements. As already discussed, the stator motor assembly may be a series of windings around a motor iron (assembly of ferromagnetic laminations) that is subsequently potted in a thermally conductive and electrical insulative potting material.

The four-pole motor according to the preferred embodiment provides for substantially continuous winding connecting the windings of each pole with a minimal number of soldered or crimped terminations. In such configuration, the motor assembly includes three phases with four interconnected windings per phase for a total of 12 windings wrapped around a torrid motor iron (i.e., laminate assembly). As the motor is controlled and the windings are energized, this creates a magnetic field that interacts with motor magnets of the rotor for affecting a torque on the rotor and providing rotational motion. According to the preferred embodiment, supercritical operation at speeds in the range of 15,000 RPM or more can be expected.

Although the present invention has been described herein with reference to a particular embodiment, it will be understood that this description is exemplary in nature and is not considered as a limitation on the scope of the invention. The scope and spirit of the present invention is therefore broad as to encompass all novel aspects of the invention taken apart or combined together in various configurations as can be envisioned in the full context of this disclosure.

The invention claimed is:

1. A blood pump, comprising:
an annular flow path defined between an inner surface of a housing and an outer surface of a rotor;
an inflow end of the flow path providing for entry of blood through an inflow conduit;
an outflow end of the flow path providing for exit of said blood through an outflow conduit;
the rotor including an inflow element having at least one blade, the inflow element forming a flow path divergence, an outflow element on the outflow end forming a flow path convergence, and a body extending between the inflow element and the outflow element, the inflow element, outflow element, and body each being connected to one another by a shaft;
at least one sensor coil at the flow path divergence, the at least one sensor coil being wound within a groove around at least partially around the inflow element; and
an exterior housing, the exterior housing having a dome and a cable assembly for storing the electrical interconnections within the blood pump, the cable assembly including a feed-through body, the cable assembly being parallel to and laterally offset from a central axis of the outflow conduit.

2. The pump of claim 1, wherein the inflow element is positioned at least partially in the inflow conduit.

3. The pump of claim 2, wherein the at least one blade of the inflow element is at least partially positioned in the inflow conduit.

4. The pump of claim 1, wherein the outflow element is positioned at least partially in the outflow conduit.

5. The pump of claim 1, wherein the flow path divergence directs blood flow from the inlet conduit to the annular flow path, and the flow path convergence directs the blood flow from the annular flow path to the outflow conduit.

6. The pump of claim 1, wherein the annular flow path over the inflow element, body and outflow element allows for minimal blood damage or thrombus formation.

7. The pump of claim 1, wherein a width of the annular flow path is approximately equivalent to a width of the inflow and outflow conduits.

8. The pump of claim 1, wherein the cable assembly is protected by an elastic strain relief boot.

9. The pump of claim 8, wherein the elastic strain relief boot is clamped to an underlying connector structure with retention rings.

* * * * *